(12) United States Patent
Hayashi et al.

(10) Patent No.: US 10,398,694 B2
(45) Date of Patent: Sep. 3, 2019

(54) MULTI-LAYERED TABLET CONTAINING DRUG UNSTABLE TO LIGHT

(71) Applicant: Shionogi & Co., Ltd., Osaka (JP)

(72) Inventors: Kentaro Hayashi, Hyogo (JP); Toshitada Toyoda, Hyogo (JP); Yoshitsugu Muguruma, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/585,903

(22) Filed: May 3, 2017

(65) Prior Publication Data

US 2017/0231989 A1    Aug. 17, 2017

Related U.S. Application Data

(63) Continuation of application No. PCT/JP2015/081526, filed on Nov. 10, 2015.

(30) Foreign Application Priority Data

Nov. 11, 2014  (JP) ................. 2014-228516

(51) Int. Cl.
| | | |
|---|---|---|
| A61K 31/505 | (2006.01) | |
| A61K 9/06 | (2006.01) | |
| A61K 9/28 | (2006.01) | |
| A61K 9/20 | (2006.01) | |
| A61K 9/00 | (2006.01) | |

(52) U.S. Cl.
CPC .......... A61K 31/505 (2013.01); A61K 9/0056 (2013.01); A61K 9/2009 (2013.01); A61K 9/2086 (2013.01); A61K 9/2813 (2013.01)

(58) Field of Classification Search
None
See application file for complete search history.

(56) References Cited

U.S. PATENT DOCUMENTS 6,316,460 B1 * 11/2001 Creekmore .......... A61K 9/2009
                                                        514/256
6,548,513 B1    4/2003 Creekmore et al.
2012/0321712 A1* 12/2012 Creekmore ............ A61K 9/167
                                                        424/480

FOREIGN PATENT DOCUMENTS

| | | |
|---|---|---|
| EP | 0547000 | 12/1992 |
| EP | 1923074 | 5/2008 |
| EP | 2063868 | 11/2010 |
| EP | 2382971 | 11/2011 |
| EP | 2433652 | 3/2012 |
| EP | 2647381 | 10/2013 |
| JP | 2774037 | 9/1998 |
| JP | 2001-206877 | 7/2001 |
| JP | 3267960 | 3/2002 |
| JP | 2005-518360 | 6/2005 |
| JP | 3815301 | 3/2006 |
| JP | 2009545561 | 12/2009 |
| JP | 2010-503723 | 2/2010 |
| JP | 4800467 | 10/2011 |
| JP | 4800988 | 10/2011 |
| JP | 2012-144564 | 8/2012 |
| JP | 2013-35797 | 2/2013 |
| JP | 2013-133291 | 7/2013 |
| JP | 2013-216701 | 10/2013 |
| WO | 0154668 | 8/2001 |
| WO | 0154669 | 8/2001 |
| WO | 03045355 | 6/2003 |
| WO | 2007018192 | 2/2007 |
| WO | 2008015221 | 2/2008 |
| WO | 2008035128 | 3/2008 |
| WO | 2009156796 | 12/2009 |
| WO | 2010030201 | 3/2010 |
| WO | 2010087462 | 8/2010 |
| WO | 2010134540 | 11/2010 |
| WO | 2012056509 | 5/2012 |
| WO | 2012057103 | 5/2012 |
| WO | 2012074110 | 6/2012 |

OTHER PUBLICATIONS

International Search Report issued in International Application No. PCT/JP2015/081526 dated Feb. 2, 2016 (2 pages).

* cited by examiner

*Primary Examiner* — Ernst V Arnold
*Assistant Examiner* — Kyung S Chang
(74) *Attorney, Agent, or Firm* — Hamre, Schumann, Mueller & Larson, P.C.

(57) ABSTRACT

An oral disintegrating tablet which contains rosuvastatin or a salt thereof and is stable to light is provided. An oral disintegrating tablet stable to light, temperature and humidity can be provided by preparing a multi-layered tablet containing rosuvastatin or a pharmaceutically acceptable salt thereof as an active ingredient, a light stabilizer, and an inorganic salt or a basic oxide.

17 Claims, No Drawings

US 10,398,694 B2

MULTI-LAYERED TABLET CONTAINING DRUG UNSTABLE TO LIGHT

TECHNICAL FIELD

The present invention relates to a tablet, preferably an oral disintegrating tablet, stable to light and temperature and/or humidity by preparing a two-layered tablet, a three-layered tablet and a multi-layered tablet containing (E)-7-[4-(4-fluorophenyl)-6-isopropyl-2-[methyl(methylsulfonyl)amino]pyrimidin-5-yl]-(3-R,5S)-3,5-dihydroxyhept-6-enoic acid or a pharmaceutically acceptable salt thereof (rosuvastatin or a salt thereof), especially calcium salt of rosuvastatin (rosuvastatin calcium), as an active ingredient, a light stabilizer, and an inorganic salt or a basic oxide.

BACKGROUND ART (E)-7-[4-(4-Fluorophenyl)-6-isopropyl-2-[methyl(methylsulfonyl)amino]pyrimidin-5-yl]-(3R,5S)-3,5-dihydroxyhept-6-enoic acid or a pharmaceutically acceptable salt thereof (rosuvastatin or a salt thereof), especially calcium salt of rosuvastatin (rosuvastatin calcium: monocalcium bis((3R,5S,6E)-7-{4-(4-fluorophenyl)-6-isopropyl-2-[methanesulfonyl(methyl)amino]pyrimidin-5-yl}-3,5-dihydroxyhept-6-enoate))) is described as an inhibitor of 3-hydroxy-3-methylglutaryl CoA reductase (HMG CoA reductase) in European Patent Application No. 0521471 and Bioorganic and Medicinal Chemistry (1997), 5 (2), p. 437-444 and is useful for the treatment of hypercholesterolemia, hyperlipoproteinemia and atherosclerosis.

Rosuvastatin, especially rosuvastatin calcium, is decomposed under given conditions, especially by light or temperature and/or humidity. This makes it difficult to prepare the product into drugs and to obtain a pharmaceutical composition having a favorable storage period.

Examples of literatures of compositions stabilizing rosuvastatin include the following literatures: Patent Document 1 describes a pharmaceutical composition containing rosuvastatin and tribasic phosphate as a stabilizer; Reference 2 describes a pharmaceutical composition containing amorphous rosuvastatin and magnesium hydroxide and/or calcium acetate as a stabilizer; and Reference 3 describes a composition comprising a hypromellose-coated core tablet containing rosuvastatin and a stabilizer. However, even the compositions of these literatures are not sufficiently stabilized against light or temperature and/or humidity.

A dry-coated tablet comprising an inner core tablet containing a drug unstable to light, and an outer layer surrounding the inner core tablet is disclosed as a dosage form protecting a drug unstable to light (References 4 to 6). However, its manufacturing method is very complicated because it is necessary to temporarily manufacture a tablet by tableting the outer layer, and place the inner core tablet on the tablet of the outer layer, followed by compression again. Also, due to the trouble of a tableting machine, the inner core tablet may be displaced from its normal position, or a plurality of inner core tablets may be contained.

In the case of containing drugs unstable to each other, the drugs may be contained in different layers in the form of a multi-layered tablet (References 7 to 9). However, none of these literatures disclose that the preparation can be applied to a drug unstable to light or temperature.

In order to protect a drug unstable to light, a preparation containing the drug may be coated with a light stabilizer, or the preparation may be packaged in aluminum. However, in the former case, the coating of the preparation delays the disintegration the preparation and is thus difficult to apply to a preparation having rapid disintegration, especially an oral disintegrating tablet. Also, in the latter case, there is a possibility that packaging cost is increased, or a packaging step is complicated.

PRIOR ART

Patent Document

Patent Document 1: JP-A No. 2001-206877
Patent Document 2: JP-A No. 2010-503723
Patent Document 3: International Publication No. WO2010/030201
Patent Document 4: International Publication No. WO2010/087462
Patent Document 5: International Publication NO. WO2010/134540
Patent Document 6: JP-A No. 2013-133291
Patent Document 7: International Publication No. WO2012/074110
Patent Document 8: JP-A No. 2005-518360
Patent Document 9: JP-A No. 2009-545561

DISCLOSURE OF INVENTION

Problems to be Solved by the Invention

Accordingly, there has been a demand for an oral disintegrating tablet of rosuvastatin or a salt thereof, especially calcium salt of rosuvastatin, which is stable to light and temperature and/or humidity.

Means to Solve the Problems

The present inventors intensively studied to develop an oral disintegrating tablet of rosuvastatin which is stable to light and temperature and/or humidity and disintegrates rapidly in an oral cavity, and consequently completed the present invention by finding out the optimum formulation. Specifically, the formulation is a multi-layered tablet having a two-layered structure consisting of an active ingredient layer containing an active ingredient rosuvastatin or salt thereof, and an outer layer adjacent to the active ingredient layer, or a multi-layered tablet comprising an active ingredient layer containing an active ingredient rosuvastatin or salt thereof, and outer layers sandwiching the active ingredient layer.

That is, the present invention relates to:
(1) a multi-layered tablet comprising (E)-7-[4-(4-fluorophenyl)-6-isopropyl-2-[methyl(methylsulfonyl)amino]pyrimidin-5-yl]-(3-R,5S)-3,5-dihydroxyhept-6-enoic acid or a pharmaceutically acceptable salt thereof as an active ingredient, a light stabilizer, and an inorganic salt or a basic oxide,
(2) the multi-layered tablet according to the above (1), which has a two-layered structure consisting of an active ingredient layer containing the active ingredient, and an outer layer adjacent to the active ingredient layer,
(3) the multi-layered tablet according to the above (1), which comprises an active ingredient layer containing the active ingredient, and outer layers sandwiching the active ingredient layer,
(4) the multi-layered tablet according to the above (3), which has a three-layered structure,
(5) the multi-layered tablet according to any of the above (2) to (4), wherein the light stabilizer is contained in the active ingredient layer, (6) the multi-layered tablet according to any of the above (2) to (4), wherein the inorganic salt or the basic oxide is contained in the active ingredient layer,
(7) the multi-layered tablet according to any of the above (2) to (4), wherein the light stabilizer and the inorganic salt or the basic oxide are contained in the active ingredient layer,
(8) the multi-layered tablet according to any of the above (2) to (4), wherein the light stabilizer is contained in at least one outer layer,
(9) the multi-layered tablet according to any of the above (2) to (4), wherein the light stabilizer and the inorganic salt or the basic oxide are the active ingredient layer contains, and at least one outer layer contains the light stabilizer,
(10) the multi-layered tablet according to any of the above (1) to (9), wherein the light stabilizer is one or more selected from the group consisting of food tar dye, food laked tar dye, natural food dye, ferric oxide and titanium oxide,
(11) the multi-layered tablet, according to the above (10), wherein the light stabilizer is one or more selected from the group consisting of Food Red No. 2, Food Red No. 3, Food Red No. 102, Food Red No. 104, Food Red No, 105, Food Red No. 106, Food Yellow No. 4, Food Yellow No. 5, Food Green No, 3, Food Blue No, 1, Food Blue No, 2, Food Red No. 3 aluminum lake, Food Yellow No. 4 aluminum lake. Food Yellow No. 5 aluminum lake, Food Blue No. 1 aluminum lake, Food Blue No. 2 aluminum lake, carmine, copper chlorophyllin sodium, copper chlorophyll, colcothar, red ferric oxide, yellow ferric oxide, black oxide of iron, yellow oxide of iron and titanium oxide,
(12) the multi-layered tablet according to the above (10), wherein the light stabilizer is one or more selected from the group consisting of red ferric oxide, yellow ferric oxide, black oxide of iron, yellow oxide of iron and titanium oxide,
(13) the multi-layered tablet, according to the above (10), wherein the light stabilizer is yellow ferric oxide,
(14) the multi-layered tablet according to any of the above (1) to (10), wherein the inorganic salt or the basic oxide is one or more selected from the group consisting of magnesium oxide, magnesium hydroxide, magnesium carbonate, aluminum magnesium, hydroxide, aluminum hydroxide, aluminum hydroxide gel, aluminum hydroxide-sodium, hydrogen carbonate coprecipitates, sodium hydroxide, calcium silicate, tribasic calcium phosphate, calcium acetate, calcium gluconate, calcium glycerophosphate, calcium carbonate, anhydrous sodium carbonate, sodium carbonate hydrate and sodium citrate hydrate,
(15) the multi-layered tablet according to the above (14), wherein the inorganic salt or the basic oxide is magnesium oxide,
(16) the multi-layered tablet according to any of the above (1) to (15), wherein the light stabilizer is yellow ferric oxide, and the inorganic salt or the basic oxide is magnesium oxide,
(17) the multi-layered tablet according to any of the above (1) to (16), wherein the active ingredient is calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid, and
18) the multi-layered tablet according to any of the above (1) to (17), which is an oral disintegrating tablet.

Effect of the Invention

The oral disintegrating tablet of the present invention (hereinafter, referred to as the "present preparation") is an oral disintegrating tablet that enhances stability to light and temperature, also has high tablet hardness, and furthermore has a rapid oral disintegration time.

BEST MODE FOR CARRYING OUT THE INVENTION

In the present description, the active ingredient (drug) is (E)-7-[4-(4-fluorophenyl)-6-isopropyl-2-[methyl(methylsulfonyl)amino]pyrimidin-5-yl]-(3R,5S)-3,5-dihydroxyhept-6-enoic acid or a pharmaceutically acceptable salt thereof (hereinafter, also referred to as "rosuvastatin"), especially calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid (hereinafter, also referred to as "rosuvastatin calcium"). This compound is described in European Patent Application No. 0521471 and Bioorganic and Medicinal Chemistry (1997).

A content of the active ingredient (drug) in the present preparation may be an amount at which the drug efficacy is obtained. For example, the content is 0.01 to 90% by weight, preferably 0.025 to 80% by weight, more preferably 0.05 to 70% by weight based on a total amount of the preparation. When the content is more than these amounts, there is a possibility that the disintegration of the tablet is slowed, and when the content is less than these amounts, there is a possibility that a preparation becomes larger, or large amounts of tablets must be taken.

In the present description, it is preferred that the structure of the preparation should be a multi-layered tablet, for improving the light stability of rosuvastatin or a pharmaceutically acceptable salt thereof. The multi-layered tablet is a tablet having two or more layers of layer components. The structure of the present preparation is 1) a two-layered structure consisting of an active ingredient layer containing the active ingredient rosuvastatin or pharmaceutically acceptable salt thereof, and an outer layer adjacent to the active ingredient layer, or 2) a three-layered or more multi-layered structure comprising an active ingredient layer containing the active ingredient rosuvastatin or pharmaceutically acceptable salt thereof, and outer layers sandwiching the active ingredient layer. The multi layered structure is preferably a three-layered structure comprising an active ingredient layer containing the active ingredient rosuvastatin or pharmaceutically acceptable salt thereof, and outer layers sandwiching the active ingredient layer. Also, the active ingredient layer and the outer layer may contain an additional active ingredient other than rosuvastatin. A content of the active ingredient layer is 20 to 80% by weight, preferably 30 to 70% by weight, more preferably 40 to 60% by weight based on a total amount of the preparation. A content of the outer layer is a remaining content determined by subtracting the content of the active ingredient layer from a total amount of the preparation.

The present preparation contains a light stabilizer in order to improve the light stability of rosuvastatin or a pharmaceutically acceptable salt thereof. The light stabilizer may be contained in any layer of the preparation having a multi-layered structure and may be preferably contained in the active ingredient layer containing the active ingredient.

In the present description, the light stabilizer may be an additive agent that can stabilize rosuvastatin, especially rosuvastatin calcium, against light, and those described in Japanese Pharmacopoeia, Pharmaceutical Standards outside the Japanese Pharmacopoeia, Japanese Pharmaceutical Excipients and Japanese Standard of Food Additives may be used. Examples include food tar dye, food laked tar dye, natural food dye, ferric oxide and titanium oxide. Preferably, examples include Food Red No. 2, Food Red No. 3, Food Red No. 102. Food Red No. 104, Food Red No. 105. Food Red No, 106, Food Yellow No. 4, Food Yellow No. 5, Food Green No. 3, Food Blue No. 1. Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, red ferric oxide, yellow ferric oxide, black oxide of iron, yellow oxide of iron and titanium oxide. The light stabilizer is more preferably red ferric oxide, yellow ferric oxide, black oxide of iron, yellow oxide of iron and/or titanium oxide, particularly preferably yellow ferric oxide.

In the present description, a content of the light stabilizer may be an amount at which rosuvastatin, especially rosuvastatin calcium, is stabilized against light. For example, the content is 0.01 to 80% by weight, preferably 0.025 to 70% by weight, more preferably 0.05 to 50% by weight based on a total amount of the preparation. When the content is more than these amounts, there is a possibility that a preparation cannot be manufactured, and when the content is less than these amounts, there is a possibility that stabilization against light is insufficient.

The present preparation contains an inorganic salt or a basic oxide in order to improve the stability of rosuvastatin or a pharmaceutically acceptable salt thereof to temperature and/or humidity. The inorganic salt is a salt or a mineral that is formed by replacing hydrogen of an inorganic acid with a metal. The basic oxide is an oxide of a metal element that forms a base through reaction with water or forms a salt through reaction with an acid. The inorganic salt or the basic oxide may be contained in any layer of the preparation having a multi-layered structure and may be preferably contained in the active ingredient layer containing the active ingredient.

In the present description, the inorganic salt or the basic oxide may be an additive agent that stabilizes rosuvastatin, especially rosuvastatin calcium, and those described in Japanese Pharmacopoeia, Pharmaceutical Standards outside the Japanese Pharmacopoeia, Japanese Pharmaceutical Excipients and Japanese Standard of Food Additives may be used. The inorganic salt or the basic oxide is, for example, magnesium oxide, magnesium hydroxide, magnesium carbonate, aluminum magnesium hydroxide, aluminum hydroxide, aluminum hydroxide gel, aluminum hydroxide-sodium hydrogen carbonate coprecipitates, sodium hydroxide, calcium silicate, tribasic calcium phosphate, calcium acetate, calcium gluconate, calcium glycerophosphate, calcium carbonate, anhydrous sodium carbonate, sodium carbonate hydrate and for sodium citrate hydrate. The inorganic salt or the basic oxide is preferably magnesium oxide.

In the present description, a content of the inorganic salt or the basic oxide may be an amount at which rosuvastatin, especially rosuvastatin calcium, is stabilized against temperature and moisture (humidity). For example, the content is 0.01 to 80% by weight, preferably 0.025 to 70% by weight, more preferably 0.05 to 50% by weight based on a total amount of the preparation. When the content is more than these amounts, there is a possibility that a preparation cannot be manufactured, and when the content is less than these amounts, there is a possibility that stabilization, especially stabilization under high temperature and high humidity, cannot be attained.

In the present preparation, the light stabilizer and the inorganic salt or the basic oxide may be used in combination. A preferred combination is yellow ferric oxide and/or titanium oxide as the light stabilizer and magnesium oxide as, the inorganic salt or the basic oxide.

In the case of using the light stabilizer and the inorganic salt or the basic oxide in combination, a preferred combination and a content thereof are yellow ferric oxide as the light stabilizer and magnesium oxide as the inorganic salt or the basic oxide and, in this case, 0.01 to 80% by weight of yellow ferric oxide and 0.01 to 80% by weight of magnesium oxide, preferably 0.025 to 70% by weight of yellow ferric oxide and 0.025 to 70% by weight of magnesium oxide, more preferably 0.05 to 50% by weight of yellow ferric oxide and 0.05 to 50% by weight of magnesium oxide, based on a total amount of the preparation. In the case where the light stabilizer is titanium oxide, and the inorganic salt or the basic oxide is magnesium oxide, a content of this preferred combination is 0.01 to 80% by weight of titanium oxide and 0.01 to 80% by weight of magnesium oxide, preferably 0.025 to 70% by weight of titanium oxide and 0.025 to 70% by weight of magnesium oxide, more preferably 0.05 to 50% by weight of titanium oxide and 0.05 to 50% by weight of magnesium oxide, based on a total amount of the preparation. In the case where the light stabilizer is yellow ferric oxide and titanium oxide, the inorganic salt or the basic oxide is magnesium oxide, a content of this preferred combination is 0.01 to 80% by weight of yellow ferric oxide and titanium oxide and 0.01 to 80% by weight of magnesium oxide, preferably 0.025 to 70% by weight of titanium oxide and 0.025 to 70% by weight of magnesium oxide, more preferably 0.05 to 50% by weight of titanium oxide and 0.05 to 50% by weight of magnesium oxide, based on a total amount of the preparation.

The present preparation may contain a disintegrator, and those described in Japanese Pharmacopoeia, Pharmaceutical Standards outside the Japanese Pharmacopoeia, Japanese Pharmaceutical Excipients and Japanese Standard of Food Additives may be used. Examples include carmellose, crospovidone, croscarmellose sodium, carmellose calcium, carboxymethylstarch sodium, and low substituted hydroxypropylcellulose. The disintegrator is preferably carmellose.

A content of the disintegrator is, for example, 1 to 30% by weight, preferably 5 to 25% by weight, more preferably 7.5 to 20% by weight based on a total amount of the preparation. When the content is more than these amounts, there is a possibility that the hardness of a tablet is reduced, and when the content is less than these amounts, there is a possibility that the disintegration time of the tablet becomes longer.

The present preparation may contain an excipient, and those described in Japanese Pharmacopoeia, Pharmaceutical Standards outside the Japanese Pharmacopoeia, Japanese Pharmaceutical Excipients and Japanese Standard of Food Additives may be used. Examples include powdered hydrogenated maltose starch syrup, glucose, fructose, lactose, D-mannitol, erythritol, aagaltitol, trehalose, sorbitol, sucrose, saccharose, fructo-oligosaccharide, palatinose, maltose, hydrogenated maltose starch, powdered syrup, starch syrup, lactose, lactulose, hydrogenated lactose lactitol, honey sugar, D-sorbitol, xylitol, corn starch, potato starch, wheat starch, rice starch, crystal cellulose, silicic anhydride, anhydrous calcium phosphate, anhydrous calcium hydrogen phosphate, precipitated calcium carbonate and calcium silicate. The excipient is preferably anhydrous calcium hydrogen phosphate and/or microcrystalline cellulose.

A content of the excipient is, for example, 1 to 95% by weight, preferably 2.5 to 92.5% by weight, more preferably 5 to 90% by weight based on a total amount of the preparation. When the content is more than these amounts, there is a possibility that a preparation becomes larger, or large amounts of tablets must be taken, and when the content is less than these amounts, there is a possibility that a tablet cannot be manufactured.

The present preparation may contain a sweetener, and those described in Japanese Pharmacopoeia, Pharmaceutical Standards outside the Japanese Pharmacopoeia, Japanese Pharmaceutical Excipients and Japanese Standard of Food Additives may be used. Examples include aspartame, aminoacetic acid, fructose, hydrogenated maltose starch syrup, licorice, licorice extract, xylitol, dipotassium glycyrrhizinate, disodium glycyrrhizinate, dimonoammonium glycyrrhizinate, saccharin, saccharin sodium, thaumatin, glucose, powdered hydrogenated maltose starch syrup, maltitol, maltose, D-mannitol, starch syrup, sucralose, acesulfame potassium, neotame and stevia or salt thereof. The sweetener is preferably sucralose, acesulfame potassium and/or thaumatin.

A content of the sweetener is, for example, not more than 10% by weight, preferably 0.01 to 10% by weight, more preferably 0.1 to 7.5% by weight based on a total amount of the preparation. When the content is more than these amounts, there is a possibility that a tablet cannot be manufactured, and when the content is less than these amounts, there is a possibility that sweetness does not sufficiently arise.

The present preparation may contain a fluidity agent, and those described in Japanese Pharmacopoeia, Pharmaceutical Standards outside the Japanese Pharmacopoeia, Japanese Pharmaceutical Excipients and Japanese Standard of Food Additives may be used. Examples of the fluidity agent include hydrated silicon dioxide, light anhydrous silicic acid, heavy anhydrous silicic acid, titanium oxide, synthetic aluminum silicate and talc, and the fluidity agent is preferably hydrated silicon dioxide and/or light anhydrous silicic acid.

A content of the fluidity agent is, for example, 0.01 to 15% by weight, preferably 0.05 to 10% by weight, more preferably 0.1 to 7.5% by weight based on a total amount of the preparation. When the content is more than these amounts, there is a possibility that a preparation becomes larger, or large amounts of tablets must be taken, and when the content is less than these amounts, there is a possibility that a tablet cannot be manufactured.

The present preparation may contain a lubricant, and those described in Japanese Pharmacopoeia, Pharmaceutical Standards outside the Japanese Pharmacopoeia, Japanese Pharmaceutical Excipients and Japanese Standard of Food Additives may be used. Examples include sodium stearate fumarate, sucrose fatty acid ester, stearic acid, magnesium stearate, calcium stearate, talc and hydrated silicon dioxide, but preferred is magnesium stearate.

A content of the lubricant is, for example, 0.001 to 2% by weight, preferably 0.001 to 1% by weight, more preferably 0.001 to 0.8% by weight based on a total amount, of the preparation. When the content is more than these amounts, there is a possibility that tablet hardness or disintegration is reduced, and when the content is less than these amounts, there is a possibility that a tablet cannot be manufactured.

The present preparation may contain an additive agent except, those mentioned above, if necessary, and those described in Japanese Pharmacopoeia, Pharmaceutical Standards outside the Japanese Pharmacopoeia, Japanese Pharmaceutical Excipients and Japanese Standard of Food Additives may be used. Moreover, a content of these additive agents may be a certain ratio. Examples of the additive agent except those mentioned above include a perfume, a binding agent, a color agent, a taste masking agent and a coating agent.

The perfume includes those called flavoring agents, examples include sugar flavor, banana flavor, sun fix banana, orange extract, orange oil, caramel, camphor, cinnamon bark oil, spearmint oil, strawberry extract, chocolate extract, cherry flavor, sour orange oil, pine oil, mentha oil, vanilla flavor, bitter extract, fruit flavor, peppermint extract, mixture flavor, mint flavor, menthol, lemon powder, lemon oil and rose oil, and the perfume is preferably sugar flavor.

Examples of the binding agent include hydroxypropylcellulose, corn starch, pregelatinized starch, partly pregelatinized starch, acacia, powdered acacia, gelatin, agar, dextrin, pullulan, povidone, polyvinyl alcohol, microcrystalline cellulose, methylcellulose, ethylcellulose, carboxymethylethylcellulose, carmellose, carmellose sodium, hydroxyethylcellulose, hydroxyethylmethylcellulose, hydroxypropylcellulose and hypromellose.

Examples of the color agent include yellow ferric oxide, red ferric oxide, food dyes such as Food Red No. 3, Food Yellow No. 5 and Food Blue No. 1, brown oxide of iron, black oxide of iron, copper chlorophyll, copper chlorophyllin sodium, riboflavin, riboflavin butyrate and green tea powder.

Examples of the taste masking agent include ascorbic acid and a salt thereof, aspartame, sucralose, glycine, sodium chloride, magnesium chloride, hydrochloric acid, dilute hydrochloric acid, citric acid and a salt thereof (sodium citrate), anhydrous citric acid, L-glutamic acid and a salt thereof, succinic acid and a salt thereof, acetic acid, tartaric acid and a salt thereof, sodium hydrogen carbonate, fumaric acid and a salt thereof, malic acid and a salt thereof, glacial acetic acid, inosinic acid disodium and honey.

Examples of the coating agent include polyvinyl alcohol, ethylcellulose, carboxymethylethylcellulose, carmellose, carmellose sodium, hydroxyethylcellulose, hydroxyethylmethylcellulose, hydroxypropylcellulose, hydroxypropylmethylcellulose, PVA copolymer, acrylic acid ethyl-methyl methacrylate copolymer dispersion liquid, amino alkyl methacrylate copolymer, Opadry, carnauba wax, carboxy vinyl polymers, dry methacrylate copolymer, dimethylamino ethyl methacrylate-methyl methacrylate copolymer, stearyl alcohol, shellac, cetanol, hydroxypropylmethylcellulose acetate succinate, hydroxypropylmethylcellulose phthalate, fumarate-stearic acid-polyvinyl acetal diethylamino acetate-hydroxypropylmethylcellulose mixture, polyvinyl acetal diethylamino acetate, polyvinyl alcohol, methacrylate copolymer and 2-methyl-5-vinyl pyridine methyl acrylate-methacrylic acid copolymer.

A dosage form of the present preparation is a tablet regulated in General Rules for Preparations of Japanese Pharmacopoeia.

A manufacturing method of the present preparation is performed by 1) mixing a drug and additive agents and compressing the mixture (direct powder compression process), 2) mixing and granulating a drug and additive agents and compressing the granules (granule compression process), or 3) mixing and granulating additive agents and then mixing the granules with a drug, followed by compression. The manufacturing method is preferably performed by mixing a drug and additive agents and compressing the mixture. In the case of 2), the granules may be manufactured by a granulation process usually used in pharmaceutics. Examples include dry granulation process, extrusion granulation process, agitation granulation process, fluidized bed granulation process and rolling granulation process. The granules may be coated with a coating agent.

In the case of performing tableting, compression molding is performed using a single tableting machine, a rotary tableting machine or the like. For the compression molding, a lubricant, can be added by use of an ordinary compression process (internal mixing process) or an external lubrication process attaching the lubricant to a punches and a mortar of a tableting machine. An apparatus performing the external lubrication process is ELSP1-type III manufactured by Kikusui Seisaksho Ltd, or the like. A blended powder manufactured by the internal mixing process may be compression-molded by use of the external lubrication process.

Regarding molding of the present preparation, any shape can be adopted; for example, a shape of a circle, an ellipse, a sphere, a bar or a donut may be used, and further, the present preparation may be coated. In addition, impression such as a mark and a letter for improving discriminability, or a cleavage line for revision may be imparted.

A diameter of the present preparation may be a size that allows a patient to take the present preparation, and is usually 3 to 20 mm, preferably 4 to 15 mm, more preferably 5 to 10 mm.

A thickness of the present preparation may be a size that allows a patient to take the present preparation, and is usually 1 to 9 mm, preferably 1.5 to 7 mm, more preferably 1.75 to 5 mm.

Thicknesses of the active ingredient layer and the outer layer of the present preparation may be thicknesses at which the active ingredient is stable, a thickness of the active ingredient layer is usually 2.5 to 90%, preferably 5 to 85%, more preferably 10 to 80% based on a thickness of the whole, and a total thickness of the outer layer is usually 10 to 97.5%, preferably 15 to 95%, more preferably 20 to 90% based on a thickness of the whole.

The present preparation has a multi-layered structure and may contain the active ingredient, the light stabilizer, and the inorganic salt or the basic oxide in each of the outer layer and the active ingredient layer. A preferred formulation of the active ingredient, the light stabilizer, and the inorganic salt or the basic oxide is 1) a formulation in winch the light stabilizer is contained in the outer layer, and the active ingredient, the light stabilizer, and the inorganic salt or the basic oxide are contained in the active ingredient layer, 2) a formulation in which the active ingredient, the light stabilizer, and the inorganic salt or the basic oxide are contained in the active ingredient layer, 3) a formulation in which the light stabilizer and the inorganic, salt or the basic oxide are contained in the outer layer, and the active ingredient, the light stabilizer, and the inorganic salt or the basic oxide are contained in the active ingredient layer, or 4) a formulation in which the inorganic salt or the basic oxide is contained in the outer layer, and the active ingredient, the light stabilizer, and the inorganic salt or the basic oxide are contained in the active ingredient layer, whereby the active ingredient rosuvastatin or rosuvastatin calcium is stabilized.

In the case of the multi-layered structure as described above, respective contents based on a total amount of the preparation are, for example, 0.01 to 90% by weight of the active ingredient, 0.01 to 80% by weight of the light stabilizer and 0.01 to 80% by weight of the inorganic salt or the basic oxide, preferably 0.025 to 80% by weight of the active ingredient, 0.025 to 70% by weight of the light stabilizer and 0.025 to 70% by weight of the inorganic salt or the basic oxide, more preferably 0.05 to 70% by weight of the active ingredient, 0.05 to 50% by weight of the light stabilizer and 0.05 to 50% by weight of the inorganic salt or the basic oxide.

A preferred formulation of the active ingredient, the light stabilizer, and the inorganic salt or the basic oxide is 1) a formulation in which yellow ferric oxide as the light stabilizer is contained in the outer layer, and rosuvastatin calcium as the active ingredient, yellow ferric oxide as the light stabilizer, and magnesium oxide as the inorganic salt or the basic oxide are contained in the active ingredient layer, 2) a formulation in which rosuvastatin calcium as the active ingredient, yellow ferric oxide as the light stabilizer, and magnesium oxide as the inorganic salt or the basic oxide are contained in the active ingredient layer, 3) a formulation in which yellow ferric oxide as the light stabilizer and magnesium oxide as the inorganic salt or the basic oxide are contained in the outer layer, and rosuvastatin calcium as the active ingredient, yellow ferric oxide as the light stabilizer, and magnesium oxide as the inorganic salt or the basic oxide are contained in the active ingredient layer, or 4) a formulation in which magnesium oxide as the inorganic salt or the basic oxide is contained in the outer layer, and rosuvastatin calcium as the active ingredient, yellow ferric oxide as the light stabilizer, and magnesium oxide as the inorganic salt or the basic oxide are contained in the active ingredient layer, whereby the active ingredient rosuvastatin calcium is stabilized.

In the case of the multi-layered structure as described above, respective contents based on a total amount of the preparation are, for example, 0.01 to 90% by weight of rosuvastatin calcium, 0.01 to 80% by weight of yellow ferric oxide and 0.01 to 80% by weight of magnesium oxide, preferably 0.025 to 80% by weight of rosuvastatin calcium, 0.025 to 70% by weight of yellow ferric oxide and 0.025 to 70% by weight of magnesium oxide, more preferably 0.05 to 70% by weight of rosuvastatin calcium, 0.05 to 50% by weight of yellow ferric oxide and 0.05 to 50% by weight of magnesium oxide.

A preferred formulation of the active ingredient, the light stabilizer, and the inorganic salt or the basic oxide is 1) a formulation in which titanium oxide as the light stabilizer is contained in the outer layer, and rosuvastatin calcium as the active ingredient, titanium oxide as the light stabilizer, and magnesium oxide as the inorganic salt or the basic oxide are contained in the active ingredient layer, 2) a formulation in which rosuvastatin calcium as the active ingredient, titanium oxide as the light stabilizer, and magnesium oxide as the inorganic salt or the basic oxide are contained in the active ingredient layer, 3) a formulation in which titanium oxide as the light stabilizer and magnesium oxide as the inorganic salt or the basic oxide are contained in the outer layer, and rosuvastatin calcium as the active ingredient, titanium oxide as the light stabilizer, and magnesium oxide as the inorganic salt or the basic oxide are contained in the active ingredient layer, or 4) a formulation in which magnesium oxide as the inorganic salt or the basic oxide is contained in the outer layer, and rosuvastatin calcium as the active ingredient, titanium oxide as the light stabilizer, and magnesium oxide as the inorganic salt or the basic oxide are contained in the active ingredient layer, whereby the active ingredient rosuvastatin calcium is stabilized.

In the case of the multi-layered structure as described above, respective contents based on a total amount of the preparation are, for example, 0.01 to 90% by weight of rosuvastatin calcium, 0.01 to 80% by weight of titanium oxide and 0.01 to 80% by weight of magnesium oxide, preferably 0.025 to 80% by weight of rosuvastatin calcium, 0.025 to 70% by weight of titanium oxide and 0.025 to 70% by weight of magnesium oxide, more preferably 0.05 to 70% by weight of rosuvastatin calcium, 0.05 to 50% by weight of titanium oxide and 0.05 to 50% by weight of magnesium oxide.

A preferred formulation of the active ingredient, the light stabilizer, and the inorganic salt or the basic oxide is 1) a formulation in which yellow ferric oxide as the light stabilizer is contained in the outer layer, and rosuvastatin calcium as the active ingredient, titanium oxide as the light stabilizer, and magnesium oxide as the inorganic salt or the basic oxide are contained in the active ingredient layer, 2) a formulation in which yellow ferric oxide as the light stabilizer and magnesium oxide as the inorganic salt or the basic oxide are contained in the outer layer, and rosuvastatin calcium as the active ingredient, titanium oxide as the light stabilizer, and magnesium oxide as the inorganic salt or the basic oxide are contained in the active ingredient layer, 3) a formulation in which titanium oxide as the light stabilizer is contained in the outer layer, and rosuvastatin calcium as the active ingredient, yellow ferric oxide as the light stabilizer, and magnesium oxide as the inorganic salt or the basic oxide are contained in the active ingredient layer, or 4) a formulation in which titanium oxide as the light stabilizer and magnesium oxide as the inorganic salt or the basic oxide are contained in the outer layer, and rosuvastatin calcium as the active ingredient, yellow ferric oxide as the light stabilizer, and magnesium oxide as the inorganic salt or the basic oxide are contained in the active ingredient layer, whereby the active ingredient rosuvastatin calcium is stabilized.

In the case of the multi-layered structure as described above, respective contents based on a total amount of the preparation are, for example, 0.01 to 90% by weight of rosuvastatin calcium, 0.01 to 80% by weight of titanium oxide and yellow ferric oxide and 0.01 to 80% by weight of magnesium oxide, preferably 0.025 to 80% by weight of rosuvastatin calcium, 0.025 to 70% by weight of titanium oxide and yellow ferric oxide and 0.025 to 70% by weight of magnesium oxide, more preferably 0.05 to 70% by weight of rosuvastatin calcium, 0.05 to 50% by weight of titanium oxide and yellow ferric oxide and 0.05 to 50% by weight of magnesium oxide.

A preferred formulation of the active ingredient, the light stabilizer, and the inorganic salt or the basic oxide is 1) a formulation in which yellow ferric oxide and titanium oxide as the light stabilizer are contained in the outer layer and rosuvastatin calcium as the active ingredient, yellow ferric oxide and titanium oxide as the light stabilizer, and magnesium oxide as the inorganic salt or the basic oxide are contained in the active ingredient layer, 2) a formulation in which ferric oxide and titanium oxide as the light stabilizer are contained in the cuter layer, and rosuvastatin calcium as the active ingredient, yellow ferric oxide as the light stabilizer, and magnesium oxide as the inorganic salt or the basic oxide are contained in the active ingredient layer, 3) a formulation in which yellow ferric oxide and titanium oxide as the light stabilizer are contained in the outer layer, and rosuvastatin calcium as the active ingredient, titanium oxide as the light stabilizer, and magnesium oxide as the inorganic salt or the basic oxide are contained in the active ingredient layer, 4) a formulation in which yellow ferric oxide and titanium oxide as the light stabilizer and magnesium oxide as the inorganic salt or the basic oxide are contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 5) a formulation in which yellow ferric oxide and titanium oxide as the light stabilizer and magnesium oxide as the inorganic salt or the basic oxide are contained in the outer layer, and rosuvastatin calcium as the active ingredient, yellow ferric oxide as the light stabilizer, and magnesium oxide as the inorganic salt or the basic oxide are contained in the active ingredient layer, 6) a formulation in which yellow ferric oxide and titanium oxide as the light stabilizer and magnesium oxide as the inorganic salt or the basic oxide are contained in the outer layer, and rosuvastatin calcium as the active ingredient, titanium oxide as the light stabilizer, and magnesium oxide as the inorganic salt or the basic oxide are contained in the active ingredient layer, 7) a formulation in which rosuvastatin calcium as the active ingredient, yellow ferric oxide and titanium oxide as the light stabilizer, and magnesium oxide as the inorganic salt or the basic oxide are contained in the active ingredient layer, 8) a formulation in which yellow ferric oxide as the light stabilizer is contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 9) a formulation in which titanium oxide as the light stabilizer is contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 10) a formulation in which yellow ferric oxide as the light stabilizer and magnesium oxide as the inorganic salt or the basic oxide are contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 11) a formulation in which titanium oxide as the light stabilizer and magnesium oxide as the inorganic salt or the basic oxide are contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 12) a formulation in which magnesium oxide as the inorganic salt or the basic oxide is contained in the outer layer, and rosuvastatin calcium as the active ingredient, yellow ferric oxide and titanium oxide as the light stabilizer, and magnesium oxide as the inorganic salt or the basic oxide are contained in the active ingredient layer, 13) a formulation in which yellow ferric oxide as the light stabilizer and magnesium oxide as the inorganic salt or the basic oxide are contained in the outer layer, and rosuvastatin calcium as the active ingredient, titanium oxide as the light stabilizer, and magnesium oxide as the inorganic salt or the basic oxide are contained in the active ingredient layer, 14) a formulation in which titanium oxide as the light stabilizer and magnesium oxide as the inorganic salt or the basic oxide are contained in the outer layer, and rosuvastatin calcium as the active ingredient, yellow ferric oxide as the light stabilizer, and magnesium oxide, as the inorganic salt or the basic oxide are contained in the active ingredient layer, 15) a formulation in which yellow ferric oxide as the light stabilizer is contained in the outer layer, and rosuvastatin calcium as the active ingredient, titanium oxide as the light stabilizer, and magnesium oxide as the inorganic salt or the basic oxide are contained in the active ingredient layer, or 16) a formulation in which titanium oxide as the light stabilizer is contained in the outer layer, and rosuvastatin calcium as the active ingredient, yellow ferric oxide as the light stabilizer, and magnesium oxide as the inorganic salt or the basic oxide are contained in the active ingredient layer, whereby the active ingredient rosuvastatin calcium is stabilized.

In the case of the multi-layered structure as described above, respective contents based on a total amount of the preparation are, for example, 0.01 to 90% by weight of rosuvastatin calcium, 0.01 to 80% by weight of titanium oxide and yellow ferric oxide and 0.01 to 80% by weight of magnesium oxide, preferably 0.025 to 80% by weight of rosuvastatin calcium, 0.025 to 70% by weight of titanium oxide and yellow ferric oxide and 0.025 to 70% by weight of magnesium oxide, more preferably 0.05 to 70% by weight of rosuvastatin calcium, 0.05 to 50% by weight of titanium oxide and yellow ferric oxide, and 0.05 to 50% by weight of magnesium oxide.

A preferred formulation of the active ingredient, the light stabilizer, the inorganic salt or the basic oxide and the disintegrator is a formulation in which yellow ferric oxide as the light stabilizer and carmellose as the disintegrator are contained in the outer layer, and rosuvastatin calcium as the active ingredient, yellow ferric oxide as the light stabilizer, magnesium oxide as the inorganic salt or the basic oxide, and carmellose as the disintegrator are contained in the active ingredient layer, whereby the active ingredient rosuvastatin calcium is stabilized while an oral disintegrating tablet having high hardness and a short disintegration time can be manufactured.

In the case of the multi-layered structure as described above, respective contents based on a total amount of the preparation are, for example, 0.01 to 90% by weight of rosuvastatin calcium, 0.01 to 80% by weight of yellow ferric oxide, 0.01 to 80% by weight of magnesium oxide and 1 to 30% by weight of carmellose, preferably 0.025 to 80% by weight of rosuvastatin calcium, 0.025 to 70% by weight of yellow ferric oxide, 0.025 to 70% by weight of magnesium oxide and 5 to 25% by weight of carmellose, more preferably 0.05 to 70% by weight of rosuvastatin calcium, 0.05 to 50% by weight of titanium oxide and yellow ferric oxide, 0.05 to 50% by weight of magnesium oxide and 7.5 to 20% by weight of carmellose.

A preferred formulation of the active ingredient, the light stabilizer, the inorganic salt or the basic oxide, the disintegrator and the excipient is a formulation in which yellow ferric oxide as the light stabilizer, carmellose as the disintegrator, and anhydrous calcium hydrogen phosphate and microcrystalline cellulose as the excipient are contained in the outer layer, and rosuvastatin calcium as the active ingredient, yellow ferric oxide as the light stabilizer, magnesium oxide as the inorganic salt or the basic oxide, carmellose as the disintegrator, and anhydrous calcium hydrogen phosphate and microcrystalline cellulose as the excipient are contained in the active ingredient layer, whereby the active ingredient rosuvastatin calcium is stabilized while an oral disintegrating tablet having high hardness and a short disintegration time can be manufactured.

In the case of the multi-layered structure as described above, respective contents based on a total amount of the preparation are, for example, 0.01 to 90% by weight of rosuvastatin calcium, 0.01 to 80% by weight of yellow ferric oxide 0.01 to 80% by weight of magnesium oxide, 1 to 30% by weight of carmellose and 1 to 95% by weight of anhydrous calcium hydrogen phosphate and microcrystalline cellulose, preferably 0.025 to 80% by weight of rosuvastatin calcium, 0.025 to 70% by weight of yellow ferric oxide, 0.025 to 70% by weight of magnesium oxide, 5 to 25% by weight of carmellose and 2.5 to 92.5% by weight of anhydrous, calcium hydrogen phosphate and microcrystalline cellulose, more preferably 0.05 to 70% by weight of rosuvastatin calcium, 0.05 to 50% by weight of yellow ferric oxide, 0.05 to 50% by weight of magnesium oxide, 7.5 to 20% by weight of carmellose and 5 to 90% by weight of anhydrous calcium hydrogen phosphate and microcrystalline cellulose.

A preferred formulation of the active ingredient, the light stabilizer, the inorganic salt or the basic oxide, the disintegrator, the excipient and the sweetener is a formulation in which yellow ferric oxide as the light stabilizer, carmellose as the disintegrator, anhydrous calcium hydrogen phosphate and microcrystalline cellulose as the excipient, and sucralose and acesulfame potassium as the sweetener are contained in the outer layer, and rosuvastatin calcium as the active ingredient, yellow ferric oxide as the light stabilizer, magnesium oxide as the inorganic, salt or the basic oxide, carmellose as the disintegrator, anhydrous calcium hydrogen phosphate and microcrystalline cellulose as the excipient, and sucralose and acesulfame potassium as the sweetener are contained in the active ingredient layer, whereby the active ingredient rosuvastatin calcium is stabilized while an oral disintegrating tablet having high hardness and a short disintegration time can be manufactured.

In the case of the multi-layered structure as described above, respective contents based on a total amount of the preparation are, for example, 0.01 to 90% by weight of rosuvastatin calcium, 0.01 to 80% by weight of yellow ferric oxide, 0.01 to 80% by weight of magnesium oxide, 1 to 30% by weight of carmellose, 1 to 95% by weight of anhydrous calcium hydrogen phosphate and microcrystalline cellulose and not more than 10% by weight of sucralose and acesulfame potassium, preferably 0.025 to 80% by weight of rosuvastatin calcium, 0.025 to 70% by weight of yellow ferric oxide, 0.025 to 70% by weight of magnesium oxide, 5 to 25% by weight of carmellose, 2.5 to 92.5% by weight of anhydrous calcium hydrogen phosphate and microcrystalline cellulose and 0.01 to 10% by weight of sucralose and acesulfame potassium, more preferably 0.05 to 70% b weight of rosuvastatin calcium, 0.05 to 50% by weight of yellow ferric oxide, 0.05 to 50% by weight of magnesium oxide, 7.5 to 20% by weight of carmellose, 5 to 90% by weight of anhydrous calcium hydrogen phosphate and microcrystalline cellulose and 0.1 to 7.5% by weight of sucralose and acesulfame potassium.

A preferred formulation of the active ingredient, the light stabilizer, the inorganic salt or the basic oxide, the disintegrator, the excipient, the sweetener and the fluidity agent is a formulation in which yellow ferric oxide as the light stabilizer, carmellose as the disintegrator, anhydrous calcium hydrogen phosphate and microcrystalline cellulose as the excipient, sucralose and acesulfame potassium as the sweetener, and light anhydrous silicic acid as the fluidity agent are contained in the outer layer, and rosuvastatin calcium as the active ingredient, yellow ferric oxide as the light stabilizer, magnesium oxide as the inorganic salt or the basic oxide, carmellose the disintegrator, anhydrous calcium hydrogen phosphate and microcrystalline cellulose as the excipient, sucralose and acesulfame potassium as the sweetener, and light anhydrous silicic acid as the fluidity agent are contained in the active ingredient layer, whereby the active ingredient rosuvastatin calcium is stabilized while an oral disintegrating tablet having high hardness and a short disintegration time can be manufactured.

In the case of the multi-layered structure as described above, respective contents based on a total amount of the preparation are, for example, 0.01 to 98% by weight of rosuvastatin calcium, 0.01 to 80% by weight of yellow ferric oxide, 0.01 to 80% by weight of magnesium oxide, 1 to 30% by weight of carmellose, 1 to 95% by weight of anhydrous calcium hydrogen phosphate and microcrystalline cellulose, not more than 10% by weight of sucralose and acesulfame potassium and 0.01 to 15% by weight of light anhydrous silicic acid, preferably 0.025 to 80% by weight of rosuvastatin calcium, 0.025 to 70% by weight of yellow ferric oxide, 0.025 to 70% by weight of magnesium oxide, 5 to 25% by weight of carmellose, 2.5 to 92.5% by weight of anhydrous calcium hydrogen phosphate and microcrystalline cellulose, 0.01 to 10% by weight of sucralose and acesulfame potassium and 0.1 to 10% by weight of light anhydrous silicic acid, more preferably 0.05 to 70% by weight of rosuvastatin calcium, 0.05 to 50% by weight of yellow ferric oxide, 0.05 to 50% by weight of magnesium oxide, 7.5 to 20% by weight of carmellose, 5 to 90% by weight of anhydrous calcium hydrogen phosphate and microcrystalline cellulose, 0.1 to 7.5% by weight of sucralose and acesulfame potassium and 0.2 to 7.5% by weight of light anhydrous silicic acid.

A preferred formulation of the active ingredient, the light stabilizer, the inorganic salt or the basic oxide, the disintegrator, the excipient, the sweetener, the fluidity agent and the lubricant is a formulation in which yellow ferric oxide as the light stabilizer, carmellose as the disintegrator, anhydrous calcium hydrogen phosphate and microcrystalline cellulose as the excipient, sucralose and acesulfame potassium as the sweetener, light anhydrous silicic acid as the fluidity agent, and magnesium stearate as the lubricant are contained in the outer layer, and rosuvastatin calcium as the active ingredient, yellow ferric oxide as the light stabilizer, magnesium oxide as the inorganic salt or the basic oxide, carmellose as the disintegrator, anhydrous calcium hydrogen phosphate and microcrystalline cellulose as the excipient sucralose and acesulfame potassium as the sweetener, light anhydrous silicic acid as the fluidity agent, and magnesium stearate as the lubricant are contained in the active ingredient layer, whereby the active ingredient rosuvastatin calcium is stabilized while an oral disintegrating tablet having high hardness and a short disintegration time can be manufactured.

In the case of the multi-layered structure as described above, respective contents based on a total amount of the preparation are, for example, 0.01 to 90% by weight of rosuvastatin calcium, 0.01 to 80% by weight of yellow ferric oxide, 0.01 to 80% by weight of magnesium oxide, 1 to 30% by weight of carmellose, 1 to 95% by weight of anhydrous calcium hydrogen phosphate and microcrystalline cellulose, not more than 10% by weight of sucralose and acesulfame potassium, 0.01 to 15% by weight of light anhydrous silicic acid and 0.001 to 2% by weight of magnesium stearate, preferably 0.025 to 80% by weight of rosuvastatin calcium, 0.025 to 70% by weight of yellow ferric oxide, 0.025 to 70% by weight of magnesium oxide, 5 to 25% by weight of carmellose, 2.5 to 92.5% by weight of anhydrous calcium hydrogen phosphate and microcrystalline cellulose, 0.01 to 10% by weight of sucralose and acesulfame potassium, 0.1 to 10% by weight of light anhydrous silicic acid and 0.001 to 1% by weight of magnesium stearate, more preferably 0.05 to 70% by weight of rosuvastatin calcium, 0.05 to 50% by weight of yellow ferric oxide, 0.05 to 50% by weight of magnesium oxide, 7.5 to 20% by weight of carmellose, 5 to 90% by weight of anhydrous calcium hydrogen phosphate and microcrystalline cellulose, 0.1 to 7.5% by weight of sucralose and acesulfame potassium, 0.2 to 7.5% by weight of light anhydrous silicic acid and 0.001 to 0.8% by weight of magnesium stearate.

The present preparation is useful as an oral disintegrating tablet, disintegrates rapidly in an oral cavity by saliva, and can be taken smoothly without leaving graininess. A disintegration time of the present preparation is on the order of usually 1 to 60 seconds, preferably 1 to 40 seconds, more preferably 1 to 30 seconds.

Although a value on the order of 30 to 70 N is usually known to be problem-free as to hardness (measurement value in a tablet hardness meter) of the present preparation, hardness of the oral disintegrating tablet of the present invention is on the order of 10 to 200 N, preferably 30 to 150 N.

When an oral disintegrating tablet is taken, bitterness may be felt, depending on an active ingredient. The active ingredient rosuvastatin calcium itself manifests bitterness. However, in the case of the present preparation, bitterness is hardly felt, and the present preparation may be taken by disintegration in an oral cavity, because the active ingredient layer is covered with the outer layer substantially free from the active ingredient. Moreover, bitterness is reduced by adding a sweetener or a taste masking agent into the present preparation.

In the present invention, it is also possible to manufacture in advance a preparation (e.g., powders or granules) containing the active ingredient and having reduced bitterness, and then mix the preparation with the above ingredients to manufacture a tablet. In this case, an oral disintegrating tablet having reduced bitterness may be manufactured.

The present preparation may be ken without disintegrating in an oral cavity or may be taken together with water.

EXAMPLES

The present invention will be explained in more detail below by way of Examples, Comparative Examples and Reference Examples, but these do not limit the present invention. Tablets obtained in Examples, Comparative Examples and Reference Examples were manufactured by the following methods 1. Manufacturing Process for Single-Layer Tablet Table 1 shows a tablet formulation per tablet. The drug used was rosuvastatin calcium (manufactured by AstraZeneca plc). Also, the light stabilizer used was yellow ferric oxide (manufactured by Kishi Easel Co., Ltd.), and the inorganic salt or the basic oxide used was magnesium hydroxide (manufactured by Kyowa Chemical Industry Co., Ltd.), magnesium oxide (manufactured by ICL Industrial Products) and tribasic calcium phosphate (manufactured by Innophos Inc.). Other additive agents used were microcrystalline cellulose (manufactured by Asahi Kasei Chemicals Corp.), anhydrous calcium hydrogen phosphate (manufactured by Kyowa Chemical. Industry Co., Ltd.), carmellose (manufactured by Gotoku Chemical Co., Ltd.), sucralose (manufactured by San-Ei Gen F.F.I. Inc.), acesulfame potassium (manufactured by Kirin Kyowa Foods Co., Ltd.), thaumatin (manufactured by San-Ei Gen F.F.I., Inc.), light anhydrous silicic acid (manufactured by Cabot Corp.), mentha oil (manufactured by Koshiro Co., Ltd.), orange oil (manufactured by Ogawa & Co., Ltd.) and magnesium stearate (manufactured by Mallinckrodt plc).

In the manufacturing process, rosuvastatin calcium and any of magnesium hydroxide, magnesium oxide and tribasic calcium phosphate as the inorganic salt or the basic oxide were blended with microcrystalline cellulose, anhydrous calcium hydrogen phosphate, carmellose, sucralose, acesulfame potassium, thaumatin, light anhydrous silicic acid and 1-menthol or orange oil as the flavor to produce a powder for tablets. This powder for tablets was compressed using punches and a mortar coated with magnesium stearate in a compression tester for formulation study (static compressor model ABM100S manufactured by JT Tashi, Inc.) to prepare tablets. Tablets of Comparative Example 2 were manufactured as a formulation free from the inorganic salt or the basic oxide. In this operation, the punches used had a round shape with a diameter of 6.5 mm.

2. Temperature and Humidity Stability Test

A specimen was placed in a constant temperature and humidity chamber (manufactured by Nagano Science Co., Ltd.) and stored at 40° C. under 75% relative humidity for 4, 8 or 12 weeks. Then, the amounts of lactone and other relative substances were measured using HPLC.

3. Hardness Test

Hardness was measured using a tablet hardness tester (manufactured by ERWEKA International AG). The test was conducted on two tablets, and an average value thereof is shown.

4. Oral Disintegration Test

Disintegration times of two tablets were measured using a disintegration tester according to the disintegration test of the 16th revised Japanese Pharmacopoeia (without disks, test solution: purified water). The largest disintegration time is shown in a table.

TABLE 1

(Unit: w/w %)

| | Reference Example 1 | Reference Example 2 | Reference Example 3 | Comparative Example 1 |
|---|---|---|---|---|
| Rosuvastatin calcium | 2.45 | 2.45 | 2.45 | 2.45 |
| Microcrystalline cellulose | 30.28 | 28.43 | 28.43 | 31.19 |
| Anhydrous calcium hydrogen phosphate | 45.33 | 45.41 | 45.41 | 54.40 |
| Carmellose | 9.97 | 9.99 | 9.9 9 | 9.97 |
| Magnesium hydroxide | 9.97 | 9.9 7 | — | — |
| Magnesium oxide | — | 9.9 9 | — | — |
| Tribasic calcium phosphate | — | — | 9.9 9 | — |
| Sucralose | 0.91 | 1.36 | 1.36 | 0.91 |
| Acesulfame potassium | 0.45 | 0.4 5 | 0.45 | 0.45 |
| Thaumiatin | 0.09 | — | — | 0.09 |
| Light anhydrous silicic acid | 0.36 | 1.45 | 1.45 | 0.36 |
| Mentha oil | 0.09 | — | — | 0.09 |
| Orange oil | — | 0.36 | 0.36 | — |
| Magnesium stearate | 0.09 | 0.09 | 0.09 | 0.09 |
| Sum | 100.00 | 100.00 | 100.00 | 100.00 |

5. Results of Temperature Stability Test

The amount of a primary relative substance lactone after storage at 40° C. under 75% relative humidity for 4, 8 or 12 weeks is shown in Table 2, and the amounts of other relative substances are shown in Table 3.

TABLE 2

(Unit: %)

| Storage condition | Reference Example 1 | Reference Example 2 | Reference Example 3 | Comparative Example 1 |
|---|---|---|---|---|
| 40° C., 75 % relative humidity 4w | N.D. | N.D. | 7.32 | 37.76 |
| 40° C., 75 % relative humidity 8w | N.D. | N.D. | 5.36 | 37.12 |
| 40° C., 75 % relative humidity 12w | N.D. | N.D. | 8.36 | 25.47 |

N.D.: equal to or less than detection limit

TABLE 3

(Unit: %)

| Storage condition | Reference Example 1 | Reference Example 2 | Reference Example 3 | Comparative Example 1 |
|---|---|---|---|---|
| 40° C., 75 % relative humidity 4w | 0.21 | 0.26 | 0.93 | 1.15 |
| 40° C., 75 % relative humidity 8w | 0.12 | 0.21 | 0.99 | 1.52 |
| 40° C., 75 % relative humidity 12w | 0.19 | 0.39 | 1.70 | 1.14 |

As a result, the formulations containing magnesium hydroxide Reference Example 1), magnesium oxide (Reference Example 2) or tribasic calcium phosphate (Reference Example 3) as the inorganic salt or the basic oxide, as compared with the formulation free from the inorganic salt or the basic oxide (Comparative Example 1), resulted in evidently low amounts of lactone and other relative substances. Moreover, when the amounts of lactone and other relative substances were compared between the formulations of Reference Examples 1 and 2 and the formulation of Reference Example 3, low values were obtained in Reference Examples 1 and 2.

6. Results about Single-Layer Tablet Hardness and Disintegration Time

The hardness and disintegration times of the tablets of Reference Examples 1, 2 and 3 and Comparative Example 1 are shown in Table 4. As a result, all of the tablets had hardness of not less than 30 N, and the tablets disintegrated within 30 seconds.

TABLE 4

| | Reference Example 1 | Reference Example 2 | Reference Example 3 | Comparative Example 1 |
|---|---|---|---|---|
| Tablet hardness (N) | 65.5 | 37.0 | 34.0 | 79.0 |
| Disintegration time (s) | 9.6 | 10.3 | 8.5 | 10.5 |

7. Manufacturing Process of Single-Layer Tablet Containing Light Stabilizer

Table 5 shows a tablet formulation per tablet. The drag used was rosuvastatin calcium (manufactured by AstraZeneca plc). Also, the light stabilizer used was yellow ferric oxide (manufactured by Kishi Kasei Co., Ltd.), and the inorganic salt or the basic oxide used was magnesium hydroxide (manufactured by Kyowa Chemical Industry Co., Ltd.). Other additive agents used were microcrystalline cellulose (manufactured by Asahi Kasei Chemicals Corp.), anhydrous calcium hydrogen phosphate (manufactured by Kyowa Chemical Industry Co., Ltd.), carmellose (manufactured by Gotoku Chemical Co., Ltd.), sucralose (manufactured by San-Ei Gen F.F.I., Inc.), acesulfame potassium (manufactured by Kirin Kyowa Foods Co., Ltd.), thaumatin (manufactured by San-Ei Gen F.F.I., Inc.), talc (manufactured by Fuji Talc Industrial Co., Ltd.), light anhydrous silicic acid (manufactured by Cabot Corp.), sugar flavor (manufactured by Ogawa & Co., Ltd.) and magnesium stearate (manufactured by Mallinckrodt plc).

In the manufacturing process, rosuvastatin calcium, yellow ferric oxide, magnesium hydroxide, microcrystalline cellulose, anhydrous calcium hydrogen phosphate, carmellose, sucralose, acesulfame potassium, thaumatin, talc, light anhydrous silicic acid and sugar flavor were blended to manufacture a powder for tablets. This powder for tablets was compressed using punches and a mortar coated with magnesium stearate in a compression tester for formulation study (static compressor model ABM100S manufactured by JT Toshi, Inc.) to prepare tablets. Tablets of Comparative Example 3 were manufactured as a formulation free from the light stabilizer yellow ferric oxide. In this operation, the punches used had a round shape with a diameter of 6.5 mm.

8. Light Stability Test

A specimen was placed in a large light stability testing apparatus (manufactured by Nagano Science Co., Ltd.) and irradiated with light of 3570 lux at 25° C. for 336 hours (D65 lamp, integral illuminance: 600,000 lux·hr), and the amounts of relative substances were measured using HPLC.

TABLE 5

(Unit: w/w %)

|  | Comparative Example 2 | Reference Example 4 |
|---|---|---|
| Rosuvastatin calcium | 2.45 | 2.45 |
| Microcrystalline cellulose | 30.28 | 32.27 |
| Anhydrous calcium hydrogen phosphate | 49.86 | 40.80 |
| Carmellose | 9.97 | 9.97 |
| Magnesium hydroxide | 4.99 | 4.99 |
| Sucralose | 1.36 | 1.36 |
| Acesulfame potassium | 0.45 | 0.45 |
| Thaumatin | 0.09 | 0.09 |
| Yellow ferric oxide | — | 0.27 |
| Talc | — | 6.80 |
| Light anhydrous silicic acid | 0.36 | 0.36 |
| Sugar flavor | 0.09 | 0.09 |
| Magnesium stearate | 0.09 | 0.09 |
| Sum | 100.00 | 100.00 |

9. Results of Light Stability Test

The sum of the amounts of relative substances after light irradiation is shown in Table 6. As a result, the sum of the amounts of relative substances was decreased in the formulation of Reference Example 4 containing yellow ferric oxide, as compared with the formulation of Comparative Example 2 free from yellow ferric oxide, and the sum was approximately 5%.

TABLE 6

(Unit: %)

|  | Comparative Example 2 | Reference Example 4 |
|---|---|---|
| Sum of amounts of relative substances | 12.56 | 4.86 |

10. Results about Single-Layer Tablet Hardness and Disintegration Time

The hardness and disintegration times of the tablets of Comparative Example 2 and Reference Example 4 are shown in Table 7. As a result, all of the tablets had hardness of not less than 30 N and the tablets disintegrated within 30 seconds.

TABLE 7

|  | Comparative Example 2 | Reference Example 4 |
|---|---|---|
| Tablet hardness (N) | 53.5 | 49.5 |
| Disintegration time (s) | 8.1 | 6.8 |

11. Manufacturing Process of Multi-Layered Tablet Containing Light Stabilizer

Tables 8 and 9 show a tablet formulation per tablet. The drug used was rosuvastatin calcium (manufactured by AstraZeneca plc). Also, the light stabilizer used was yellow ferric oxide (manufactured by Kishi Kasei Co., Ltd.) and titanium oxide (manufactured by Toho Titanium Co., Ltd.), and the inorganic salt or the basic oxide used was magnesium oxide (manufactured by ICL Industrial Products). Other additive agents used were microcrystalline cellulose (manufactured by Asahi Kasei Chemicals Corp.), anhydrous calcium hydrogen phosphate (manufactured by Kyowa Chemical Industry Co., Ltd.), carmellose (manufactured by Gotoku Chemical Co., Ltd.), sucralose (manufactured by San-Ei Gen F.F.I. Inc.), acesulfame potassium (manufactured by Kirin Kyowa Foods Co., Ltd.), thaumatin (manufactured by San-Ei Gen F.F.I., Inc.), light anhydrous silicic acid (manufactured by Cabot Corp.), sugar flavor (manufactured by Ogawa & Ltd.) and magnesium stearate (manufactured by Taihei Chemical Industrial Co., Ltd.).

In the manufacturing process, rosuvastatin calcium, yellow ferric oxide, titanium oxide, magnesium oxide, microcrystalline cellulose, anhydrous calcium hydrogen phosphate, carmellose, sucralose, acesulfame potassium, thaumatin, light anhydrous silicic acid and sugar flavor were blended to manufacture a blended powder for an active ingredient layer. Yellow ferric oxide, microcrystalline cellulose, anhydrous calcium hydrogen phosphate, carmellose, sucralose, acesulfame potassium, thaumatin, light anhydrous silicic acid and sugar flavor were blended to manufacture a blended powder for an outer layer. The blend powder for an outer layer, the blended powder for an active ingredient layer, and the blended powder for an outer layer were loaded in this order to punches and a mortar coated with magnesium stearate, and compressed in a compression tester for formulation study (static compressor model ABM100S manufactured by JT Toshi, Inc.) to prepare tablets. In this operation, the punches used had a round shape with a diameter of 6.5 mm for Examples 1 to 3 and a diameter of 8 mm for Examples 4 to 6.

12. Light Stability Test

A specimen was placed in a large light stability testing apparatus (manufactured by Nagano Science Co., Ltd.) and irradiated with light of 3570 lux at 25° C. for 168 hours (D65 lamp, integral illuminance: 600,000 lux·hr), and the amounts of relative substances were measured using HPLC.

TABLE 8

(Unit: w/w %)

|  |  | Example 1 | Example 2 | Example 3 |
|---|---|---|---|---|
| Outer layer | Microcrystalline cellulose | 9.42 | 9.42 | 9.42 |
|  | Anhydrous calcium hydrogen phosphate | 12.45 | 12.45 | 12.45 |
|  | Carmellose | 2.50 | 2.50 | 2.50 |
|  | Yellow ferric oxide | 0.06 | 0.06 | 0.06 |
|  | Sucralose | 0.31 | 0.31 | 0.31 |
|  | Acesulfame potassium | 0.10 | 0.10 | 0.10 |
|  | Thaumatin | 0.04 | 0.04 | 0.04 |
|  | Light anhydrous silicic acid | 0.08 | 0.08 | 0.08 |
|  | Sugar flavor | 0.02 | 0.02 | 0.02 |
|  | Magnesium stearate | 0.04 | 0.04 | 0.04 |
|  | Subtotal | 25.02 | 25.02 | 25.02 |
| Active ingredient | Rosuvastatin calcium | 2.25 | 2.25 | 2.25 |
|  | Microcrystalline cellulose | 18.26 | 18.26 | 18.26 |

TABLE 8-continued (Unit: w/w %)

|  |  | Example 1 | Example 2 | Example 3 |
|---|---|---|---|---|
|  | Anhydrous calcium hydrogen phosphate | 18.31 | 13.31 | 8.32 |
|  | Carmellose | 4.99 | 4.99 | 4.99 |
|  | Magnesium oxide | 4.99 | 4.99 | 4.99 |
|  | Titanium oxide | — | 4.99 | 9.98 |
|  | Yellow ferric oxide | 0.12 | 0.12 | 0.12 |
|  | Sucralose | 0.62 | 0.62 | 0.62 |
|  | Acesulfame potassium | 0.21 | 0.21 | 0.21 |
|  | Light anhydrous silicic acid | 0.17 | 0.17 | 0.17 |
|  | Sugar flavor | 0.04 | 0.04 | 0.04 |
|  | Subtotal | 49.96 | 49.96 | 49.96 |
| Outer layer | Microcrystalline cellulose | 9.42 | 9.42 | 9.42 |
|  | Anhydrous calcium hydrogen phosphate | 12.45 | 12.45 | 12.45 |
|  | Carmellose | 2.50 | 2.50 | 2.50 |
|  | Yellow ferric oxide | 0.06 | 0.06 | 0.06 |
|  | Sucralose | 0.31 | 0.31 | 0.31 |
|  | Acesulfame potassium | 0.10 | 0.10 | 0.10 |
|  | Thaumatin | 0.04 | 0.04 | 0.04 |
|  | Light anhydrous silicic acid | 0.08 | 0.08 | 0.08 |
|  | Sugar flavor | 0.02 | 0.02 | 0.02 |
|  | Magnesium stearate | 0.04 | 0.04 | 0.04 |
|  | Subtotal | 25.02 | 25.02 | 25.02 |
| Sum |  | 100.00 | 100.00 | 100.00 |

TABLE 9

(Unit: w/w %)

|  |  | Example 4 | Example 5 | Example 6 |
|---|---|---|---|---|
| Outer layer | Microcrystalline cellulose | 14.13 | 14.13 | 14.13 |
|  | Anhydrous calcium hydrogen phosphate | 18.70 | 18.70 | 18.70 |
|  | Carmellose | 3.74 | 3.74 | 3.74 |
|  | Yellow ferric oxide | 0.09 | 0.09 | 0.09 |
|  | Sucralose | 0.47 | 0.47 | 0.47 |
|  | Acesulfame potassium | 0.16 | 0.16 | 0.16 |
|  | Thaumatin | 0.06 | 0.06 | 0.06 |
|  | Light anhydrous silicic acid | 0.12 | 0.12 | 0.12 |
|  | Sugar flavor | 0.03 | 0.03 | 0.03 |
|  | Magnesium stearate | 0.02 | 0.02 | 0.02 |
|  | Subtotal | 37.52 | 37.52 | 37.52 |
| Active ingredient layer | Rosuvastatin calcium | 1.12 | 1.12 | 1.12 |
|  | Microcrystalline cellulose | 9.13 | 9.13 | 9.13 |
|  | Anhydrous calcium hydrogen phosphate | 9.15 | 6.65 | 4.16 |
|  | Carmellose | 2.49 | 2.49 | 2.49 |
|  | Magnesium oxide | 2.49 | 2.49 | 2.49 |
|  | Titanium oxide | — | 2.49 | 4.99 |
|  | Yellow ferric oxide | 0.06 | 0.06 | 0.06 |
|  | Sucralose | 0.31 | 0.31 | 0.31 |
|  | Acesulfame potassium | 0.10 | 0.10 | 0.10 |
|  | Light anhydrous silicic acid | 0.08 | 0.08 | 0.08 |
|  | Sugar flavor | 0.02 | 0.02 | 0.02 |
|  | Subtotal | 24.97 | 24.97 | 24.97 |
| Outer layer | Microcrystalline cellulose | 14.13 | 14.13 | 14.13 |
|  | Anhydrous calcium hydrogen phosphate | 18.70 | 18.70 | 18.70 |
|  | Carmellose | 3.74 | 3.74 | 3.74 |
|  | Yellow ferric oxide | 0.09 | 0.09 | 0.09 |
|  | Sucralose | 0.47 | 0.47 | 0.47 |
|  | Acesulfame potassium | 0.16 | 0.16 | 0.16 |
|  | Thaumatin | 0.06 | 0.06 | 0.06 |
|  | Light anhydrous silicic acid | 0.12 | 0.12 | 0.12 |
|  | Sugar flavor | 0.03 | 0.03 | 0.03 |
|  | Magnesium stearate | 0.02 | 0.02 | 0.02 |
|  | Subtotal | 37.52 | 37.52 | 37.52 |
| Sum |  | 100.00 | 100.00 | 100.00 |

13. Results of Light Stability Test

The sum of the amounts of relative substances after light, irradiation is shown in Table 10. As a result, the amount of yellow ferric oxide in the single tablets of Reference Example 4 was 0.27 w/w % whereas the total amount of yellow ferric oxide in the multilayered tablets of Examples 1 to 6 was 0.24 w/w %, and the sum of the amounts of the relative substances was able to be drastically decreased in Examples in spite of the smaller amount of yellow ferric oxide. In addition, it was revealed that the sum of the amounts of relative substances is further decreased in the formulations containing titanium oxide, though these preparations slightly whitened the tongue or an oral cavity when taken.

TABLE 10

(Unit: %)

|  | Example 1 | Example 2 | Example 3 |
|---|---|---|---|
| Sum of amounts of relative substances | 1.94 | 0.92 | 0.68 |

|  | Example 4 | Example 5 | Example 6 |
|---|---|---|---|
| Sum of amounts of relative substances | 1.87 | 0.94 | 0.79 |

14. Results about Tablet Hardness and Disintegration Time

The hardness and disintegration times of the tablets of Examples 1 to 6 are shown in Table 11. As a result, all of the tablets had hardness of not less than 30 N, and the tablets disintegrated within 30 seconds.

TABLE 11

|  | Example 1 | Example 2 | Example 3 |
|---|---|---|---|
| Tablet hardness (N) | 87.5 | 67.5 | 63.5 |
| Disintegration time (s) | 10.0 | 11.9 | 14.8 |

|  | Example 4 | Example 5 | Example 6 |
|---|---|---|---|
| Tablet hardness (N) | 139.0 | 125.5 | 121.5 |
| Disintegration time (s) | 12.1 | 25.1 | 28.0 |

15. Process for Multi-Layered Tablet Manufacturing Changing Content of Stabilizer Tables 12 and 13 show a tablet formulation per tablet. The drug used was rosuvastatin calcium (manufactured by AstraZeneca plc). Also, the light stabilizer used was yellow ferric oxide (manufactured by Kishi Kasei Co., Ltd), and the inorganic salt or the basic oxide used was magnesium oxide (manufactured by Tomita Pharmaceutical Co., Ltd.). Other additive agents used were microcrystalline cellulose (manufactured by Asahi Kasei Chemicals Corp.), anhydrous calcium hydrogen phosphate (manufactured by Kyowa Chemical Industry Co., Ltd.), carmellose (manufactured by Gotoku Chemical Co., Ltd.), sucralose (manufactured by San-Ei Gen F.F.I., acesulfame potassium (manufactured by Kirin Kyowa Foods Co., Ltd.), thaumatin (manufactured by San-Ei Gen F.F.I., Inc.), light anhydrous silicic acid (manufactured by Cabot Corp.), sugar flavor (manufactured by Ogawa & Co., Ltd.) and magnesium stearate (manufactured by Taihei Chemical Industrial Co., Ltd.).

In the manufacturing process, rosuvastatin calcium, yellow ferric oxide, magnesium oxide, microcrystalline cellulose, anhydrous calcium hydrogen phosphate, carmellose, sucralose, acesulfame potassium, thaumatin, light anhydrous silicic acid and sugar flavor were blended to manufacture a blended powder for an active ingredient layer. Yellow ferric oxide, microcrystalline cellulose, anhydrous calcium hydrogen phosphate, carmellose, sucralose, acesulfame potassium, thaumatin, light anhydrous silicic acid and sugar flavor were blended to manufacture a blended powder for an outer layer. The blended powder for an outer layer, the blended powder for an active ingredient layer, and the blended powder for an outer layer were loaded in this order to punches and a mortar coated with magnesium stearate, and compressed in a compression tester for formulation study (static compressor model ABM100S manufactured by JT Tashi, Inc) to prepare tablets. In this operation, the punches used had a round shape with a diameter of 6.5 mm for Examples 7 to 9 and Comparative Example 3.

16. Light Stability Test

The test was conducted in the same way as in Examples 1 to 6.

TABLE 12

(Unit: w/w %)

| | | Example 7 | Example 8 | Example 9 |
|---|---|---|---|---|
| Outer layer | Microcrystalline cellulose | 9.48 | 9.44 | 9.42 |
| | Anhydrous calcium hydrogen phosphate | 12.44 | 12.45 | 12.45 |
| | Carmellose | 2.49 | 2.50 | 2.50 |
| | Yellow ferric oxide | 0.02 | 0.04 | 0.06 |
| | Sucralose | 0.31 | 0.31 | 0.31 |
| | Acesulfame potassium | 0.10 | 0.10 | 0.10 |
| | Thaumatin | 0.02 | 0.02 | 0.04 |
| | Light anhydrous silicic acid | 0.08 | 0.08 | 0.08 |
| | Sugar flavor | 0.02 | 0.02 | 0.02 |
| | Magnesium stearate | 0.04 | 0.04 | 0.04 |
| | Subtotal | 25.00 | 25.00 | 25.00 |
| Active ingredient layer | Rosuvastatin calcium | 2.25 | 2.25 | 2.25 |
| | Microcrystalline cellulose | 18.37 | 18.30 | 18.26 |
| | Anhydrous calcium hydrogen phosphate | 18.29 | 18.30 | 18.30 |
| | Carmellose | 4.99 | 4.99 | 4.99 |
| | Magnesium oxide | 4.99 | 4.99 | 4.99 |
| | Yellow ferric oxide | 0.04 | 0.08 | 0.12 |
| | Sucralose | 0.62 | 0.62 | 0.62 |
| | Acesulfame potassium | 0.21 | 0.21 | 0.21 |
| | Thaumatin | | | |
| | Light anhydrous silicic acid | 0.17 | 0.17 | 0.17 |
| | Sugar flavor | 0.04 | 0.04 | 0.04 |
| | Subtotal | 50.00 | 50.00 | 50.00 |
| Outer layer | Microcrystalline cellulose | 9.48 | 9.44 | 9.42 |
| | Anhydrous calcium hydrogen phosphate | 12.44 | 12.45 | 12.45 |
| | Carmellose | 2.49 | 2.50 | 2.50 |
| | Yellow ferric oxide | 0.02 | 0.04 | 0.06 |
| | Sucralose | 0.31 | 0.31 | 0.31 |
| | Acesulfame potassium | 0.10 | 0.10 | 0.10 |
| | Thaumatin | 0.02 | 0.02 | 0.04 |
| | Light anhydrous silicic acid | 0.08 | 0.08 | 0.08 |
| | Sugar flavor | 0.02 | 0.02 | 0.02 |
| | Magnesium stearate | 0.04 | 0.04 | 0.04 |
| | Subtotal | 25.00 | 25.00 | 25.00 |
| Sum | | 100.00 | 100.00 | 100.00 |

TABLE 13

(Unit : w/w %)

| | | Comparative Example 3 |
|---|---|---|
| Outer layer | Microcrystalline cellulose | 9.48 |
| | Anhydrous calcium hydrogen phosphate | 12.45 |
| | Carmellose | 2.50 |
| | Yellow ferric oxide | — |
| | Sucralose | 0.31 |
| | Acesulfame potassium | 0.10 |
| | Thaumatin | 0.02 |
| | Light anhydrous silicic acid | 0.08 |

TABLE 13-continued (Unit : w/w %)

| | | Comparative Example 3 |
|---|---|---|
| | Sugar flavor | 0.02 |
| | Magnesium stearate | 0.04 |
| | Subtotal | 25.00 |
| Active ingredient layer | Rosuvastatin calcium | 2.25 |
| | Microcrystalline cellulose | 18.38 |
| | Anhydrous calcium hydrogen phosphate | 18.30 |
| | Carmellose | 4.99 |
| | Magnesium | 4.99 |
| | Yellow ferric oxide | — |
| | Sucralose | 0.62 |
| | Acesulfame potassium | 0.21 |
| | Thaumatin | 0.04 |
| | Light anhydrous silicic acid | 0.17 |
| | Sugar flavor | 0.04 |
| | Subtotal | 50.00 |
| Outer layer | Microcrystalline cellulose | 9.48 |
| | Anhydrous calcium | 12.45 |
| | Carmellose | 2.50 |
| | Yellow ferric oxide | — |
| | Sucralose | 0.31 |
| | Acesulfain potassium | 0.10 |
| | Thaumatin | 0.02 |
| | Light anhydrous silicic acid | 0.08 |
| | Sugar flavor | 0.02 |
| | Magnesium | 0.04 |
| | Subtotal | 25.00 |
| Sum | | 100.00 |

17. Results of Light Stability Test

The sum of the amounts of relative substances after light irradiation is shown in Table 14. As a result, in contrast to the tablets of Comparative Example 3 free from yellow ferric oxide, the sum of the amounts of relative substances was able to be drastically decreased in the tablets of Examples 7 to 9 containing not less than 0.08 w/w % of yellow ferric oxide. It was also found that a larger content of yellow ferric oxide leads to a smaller amount of relative substances produced.

TABLE 14

(Unit: %)

| | Example 7 | Example8 | Example 9 | Comparative Example 3 |
|---|---|---|---|---|
| SUM of amounts of relative substances | 3.37 | 2.68 | 2.38 | 6.21 |

Availability in the Industry

A tablet that is stable to light and temperature and/or humidity and is t a practical level can be provided as an oral disintegrating tablet containing rosuvastatin or a salt thereof. In addition, an oral disintegrating tablet can be manufactured as a combination drug of rosuvastatin or a salt thereof and an additional pharmaceutical product.

The invention claimed is:

1. An orally disintegrating multi-layered tablet comprising:
   (E)-7-[4-(4-fluorophenyl)-6-isopropyl-2-methyl(methyl-sulfonyl)amino]pyrimidin-5-yl]-(3R,5S)-3,5-dihydroxyhept-6-enoic acid, or a pharmaceutically acceptable salt thereof, as an active ingredient;
   a light stabilizer;
   an inorganic salt or a basic oxide; and
   a disintegrator,
   wherein the tablet disintegrates in an oral cavity with saliva within a disintegration time in a range from 1 to 60 seconds,
   the tablet has a two-layered molded structure or a multi-layered molded structure,
   the two-layered structure consists of an active ingredient layer comprising the active ingredient, and an outer layer adjacent to the active ingredient layer,
   the multi-layered structure comprises the active ingredient layer comprising the active ingredient, and outer layers sandwiching the active ingredient layer,
   the active ingredient layer comprises: (i) the light stabilizer, (ii) the inorganic salt or the basic oxide, and (iii) the disintegrator,
   the outer layer comprises the disintegrator,
   an amount of the active ingredient layer is in a range from 20% to 80% by weight relative to the tablet, and
   the tablet does not have a coating layer on the molded structure, wherein the light stabilizer is one or more materials selected from the group consisting of food tar dye, food laked tar dye, natural food dye, ferric oxide, black oxide of iron, yellow oxide of iron, and titanium oxide; and wherein the inorganic salt or the basic oxide is one or more materials selected from the group consisting of magnesium oxide, magnesium hydroxide, magnesium carbonate, aluminum magnesium hydroxide, aluminum hydroxide, aluminum hydroxide gel, aluminum hydroxide-sodium hydrogen carbonate coprecipitates, sodium hydroxide, calcium silicate, tribasic calcium phosphate, calcium acetate, calcium gluconate, calcium glycerophosphate, calcium carbonate, anhydrous sodium carbonate, sodium carbonate hydrate, and sodium citrate hydrate.

2. The orally disintegrating multi-layered tablet according to claim 1, which has the two-layered structure.

3. The orally disintegrating multi-layered tablet according to claim 1, which has the multi-layered structure.

4. The orally disintegrating multi-layered tablet according to claim 3, which has a three-layered structure.

5. The orally disintegrating multi-layered tablet according to claim 1, wherein the light stabilizer further is contained in at least one of the outer layers.

6. The orally disintegrating multi-layered tablet according to claim 2,
   wherein said outer layer comprises the light stabilizer.

7. The orally disintegrating multi-layered tablet according to claim 1,
   wherein the light stabilizer is one or more materials selected from the group consisting of Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, red ferric oxide, yellow ferric oxide, and titanium oxide.

8. The orally disintegrating multi-layered tablet according to claim 1, wherein the light stabilizer is one or more materials selected from the group consisting of red ferric oxide, yellow ferric oxide, black oxide of iron, yellow oxide of iron, and titanium oxide.

9. The orally disintegrating multi-layered tablet according to claim 1, wherein the light stabilizer is yellow ferric oxide.

10. The orally disintegrating multi-layered tablet according to claim 1, wherein the inorganic salt or the basic oxide is magnesium oxide.

11. The orally disintegrating multi-layered tablet according to claim 1,
wherein the light stabilizer is yellow ferric oxide, and the inorganic salt or the basic oxide is magnesium oxide.

12. The orally disintegrating multi-layered tablet according to claim 1, wherein the active ingredient is calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid.

13. The orally disintegrating multi-layered tablet according to claim 1,
wherein the multiple layers in the orally disintegrating multi-layered tablet are layers compressed together by tableting.

14. The orally disintegrating multi-layered tablet according to claim 2,
wherein the outer layer has a thickness in a range from 10 to 97.5% relative to a thickness of a whole tablet.

15. The orally disintegrating multi-layered tablet according to claim 3,
wherein the outer layers have a total thickness in a range from 10 to 97.5% relative to a thickness of a whole tablet.

16. The orally disintegrating multi-layered tablet according to claim 1,
wherein the tablet is none of
(a) a dry-coated tablet comprising an inner core tablet comprising the active ingredient, and an outer layer surrounding the inner core tablet, and
(b) a preparation comprising the active ingredient covered with a light stabilizer.

17. The orally disintegrating multi-layered tablet according to claim 1,
wherein the disintegrator in the active ingredient layer and in the outer layer is each selected from the group consisting of carmellose, crospovidone, croscarmellose sodium, carmellose calcium, carboxymethylstarch sodium, and low substituted hydroxypropylcellulose.

* * * * *